(12) United States Patent
Eriksson et al.

(10) Patent No.: US 8,187,285 B2
(45) Date of Patent: May 29, 2012

(54) METHOD AND APPARATUS FOR PROCESSING DERMAL TISSUE

(75) Inventors: Elof Eriksson, Wellesley, MA (US); Christian Baker, Weymouth, MA (US); W. Robert Allison, Sudbury, MA (US)

(73) Assignee: Applied Tissue Technologies LLC, Newton, MA (US)

( * ) Notice: Subject to any disclaimer, the term of this patent is extended or adjusted under 35 U.S.C. 154(b) by 294 days.

(21) Appl. No.: 12/603,190

(22) Filed: Oct. 21, 2009

(65) Prior Publication Data

US 2010/0042127 A1 Feb. 18, 2010

Related U.S. Application Data

(63) Continuation of application No. 10/789,620, filed on Feb. 27, 2004, now Pat. No. 7,625,384.

(60) Provisional application No. 60/450,375, filed on Feb. 27, 2003.

(51) Int. Cl.
*A61B 17/50* (2006.01)
(52) U.S. Cl. ........................................ 606/132
(58) Field of Classification Search .................. 606/131, 606/132; 30/122, 120; 15/236.01, 236.05, 15/236.06, 236.07, 236.08, 236.09, 236.1
See application file for complete search history.

(56) References Cited

U.S. PATENT DOCUMENTS

| | | | |
|---|---|---|---|
| 2,839,109 | A | 6/1958 | Wilson |
| 3,076,462 | A | 2/1963 | Meek et al. |
| 3,640,279 | A | 2/1972 | Brown et al. |
| 4,136,746 | A | 1/1979 | Tusing |
| 4,690,139 | A | 9/1987 | Rosenberg |
| 5,004,468 | A | 4/1991 | Atkinson |
| 5,196,020 | A | 3/1993 | Atkinson et al. |
| 5,964,729 | A | 10/1999 | Choi et al. |
| 6,248,114 | B1 | 6/2001 | Ysebaert |
| 6,440,143 | B2 | 8/2002 | Kasten |
| 2001/0029380 | A1 | 10/2001 | Ysebaert |
| 2004/0175690 | A1 | 9/2004 | Mishra et al. |

FOREIGN PATENT DOCUMENTS

| | | |
|---|---|---|
| CA | 2220755 | 11/1997 |
| FR | 1009467 | 1/1952 |
| FR | 1497723 | 10/1966 |
| WO | 03039382 | 5/2003 |
| WO | 2004075764 | 9/2004 |

*Primary Examiner* — Gary Jackson
*Assistant Examiner* — Michael Mendoza
(74) *Attorney, Agent, or Firm* — Quarles & Brady LLP (57) ABSTRACT

A portable and disposable device is provided for processing harvested dermal tissue. The device includes a housing presenting a handle having a gripping surface and a cutting head attached to the handle. A cutting assembly is supported by the cutting head and includes a plurality of spaced cutting blades that are rotatable with respect to the housing. A receptacle is disposed downstream of the cutting assembly and receives the sliced tissue from the cutting blades. The device is thus operable to slice harvested tissue into strips, and further into fine particles, that can be used for transplantation onto a wound site.

12 Claims, 14 Drawing Sheets

FIG. 18 ions of the which are hereby incorporated by reference in their entireties.

METHOD AND APPARATUS FOR PROCESSING DERMAL TISSUE

CROSS-REFERENCE TO RELATED APPLICATIONS

This application is a continuation of U.S. patent application Ser. No. 10/789,620 now U.S. Pat. No. 7,625,384, filed Feb. 27, 2004, which claims priority to U.S. Provisional Patent Application No. 60/450,375, filed Feb. 27, 2003, the disclosures of which are hereby incorporated by reference in their entireties.

STATEMENT REGARDING FEDERALLY SPONSORED RESEARCH OR DEVELOPMENT

Not applicable.

BACKGROUND OF THE INVENTION

The present invention relates to a method and apparatus for processing dermal tissue that has been harvested from a patient and, in particular, relates to a method and apparatus for cutting and mincing dermal tissue into particles suitable for transplantation into a wound on the patient.

Skin grafting has traditionally involved the removal of a thin slice of dermal tissue from a donor site on a patient. The slice of tissue is then used to cover the site of a wound, which is typically a non self-healing wound or a burn. In some cases the tissue is processed before it is applied to the recipient wound site. A common process called meshing creates a number of small, non-connected cuts in the slice of tissue. The tissue can then be stretched until it has the appearance of a mesh or net. In this state, it can cover a larger area of a wound. Other methods of processing include cutting the tissue into particles with knives, blades, or scissors.

The purpose of such processing is to use tissue from a donor site to cover a wound area that is larger than the donor site. The ratio of the wound area to the donor site area is called the expansion ratio. A higher expansion ratio is desirable to minimize the trauma of the donor site, and to aid patients who have only a small amount of dermal tissue available for grafting purposes.

Traditional methods of processing dermal tissue have produced low expansion ratios. They have also produced poor cosmetic outcomes in which the healed wound exhibits a rough and uneven surface.

Another device utilizes a drum carrying a plurality of parallel blades that is supported above a cutting surface. The strip of tissue is placed on the cutting surface, and the device is activated to rotate the drum and bring the blades into contact with the underlying cutting surface. The tissue is manually translated across the cutting surface to enable the blade to slice the tissue into fine strips. The strips of tissue can then be repositioned on the cutting surface to enable the blades to cut the strips into individual particles. Unfortunately, particles may accumulate in the interstices between adjacent blades and need to be manually removed using a spatula or the like. Furthermore, because the position of the blade is stationary relative to the cutting surface, the cutting operations may be rigid and difficult to perform.

It would therefore be desirable to provide a simpler processing device that is inexpensive, disposable, and easy to use compared to conventional devices. It would be further desirable to achieve higher expansion ratios than conventionally achieved in order to improve cosmetic outcomes for healed wounds.

BRIEF SUMMARY OF THE INVENTION

In accordance with one aspect of the invention, an apparatus for processing harvested dermal tissue supported on a cutting surface includes a housing that presents a handle having a gripping surface and a cutting head attached to the handle. A cutting assembly is connected to the cutting head. The cutting assembly includes a plurality of spaced apart blade tips that are configured to cut through the harvested tissue as the cutting assembly rotates along the cutting surface to produce sliced tissue.

In accordance with another aspect, a receptacle is disposed downstream of the cutting assembly and receives the particles from the cutting blades.

In accordance with another aspect, a tissue separator is provided including a base supported by the housing. A plurality of tines extend outwardly from the base and are configured to interdigitate with adjacent cutting blades. The tines remove sliced tissue lodged in the cutting assembly between adjacent blades.

The foregoing and other aspects of the invention will appear from the following description. In the description, reference is made to the accompanying drawings which form a part hereof, and in which there is shown by way of illustration, and not limitation, a preferred embodiment of the invention. Such embodiment does not necessarily represent the full scope of the invention, however, and reference must therefore be made to the claims herein for interpreting the scope of the invention.

DETAILED DESCRIPTION OF THE INVENTION

Figure 1:
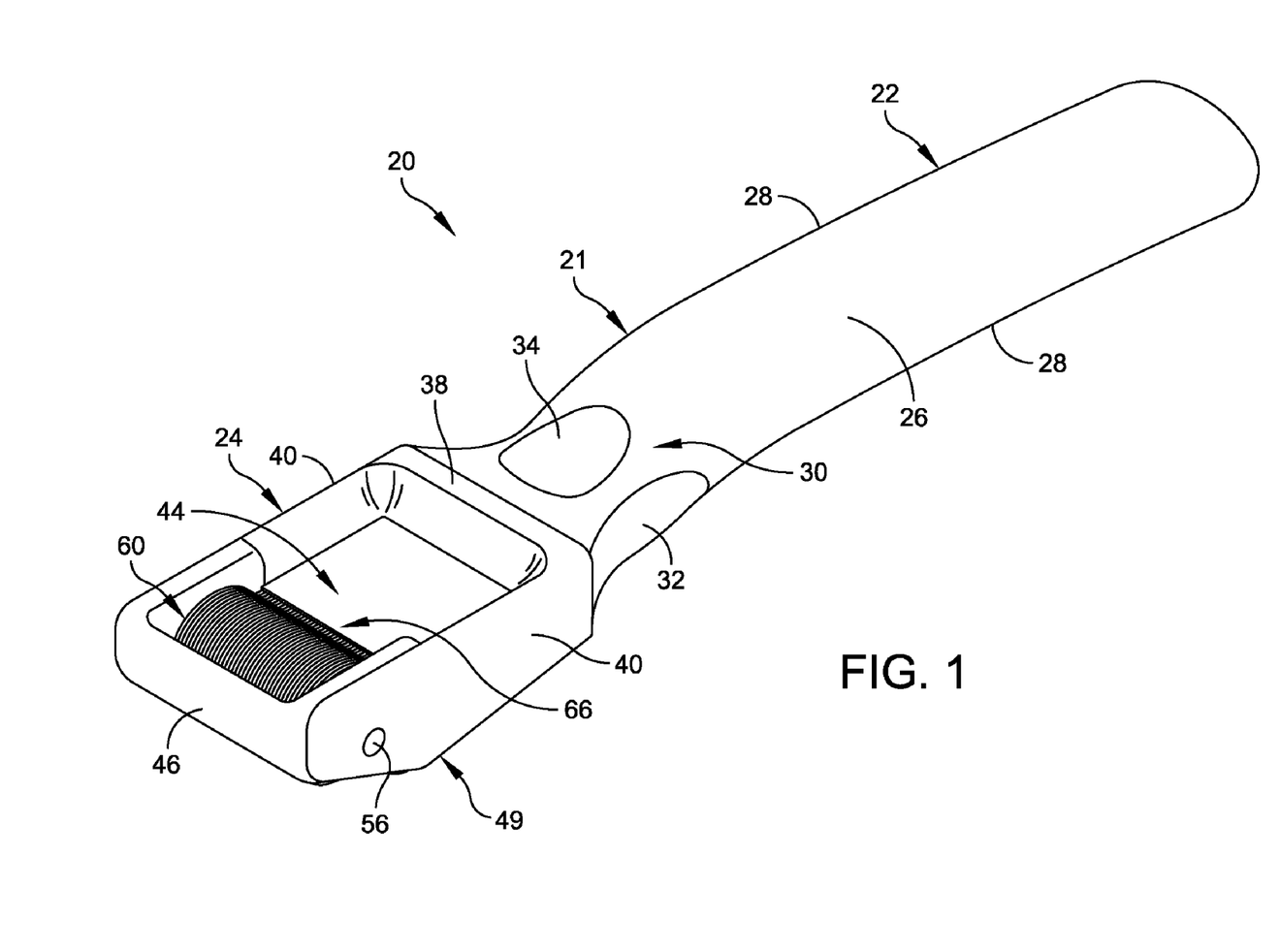
FIG. 1 is a perspective view of a harvested dermal tissue processor constructed in accordance with the preferred embodiment of the invention.

Referring to FIG. 1, a disposable, handheld device 20 for processing harvested dermal tissue includes a housing 21 presenting a substantially horizontally extending handle 22 and an interconnecting cutting head 24 extending forwardly from the handle. Handle 22 and cutting head 24 extend generally in the same plane, and are preferably formed from a plastic that is molded as an integral frame. Unless stated otherwise, device 20 can be formed from any suitable plastic, and is preferably injection or otherwise molded.

Handle 22 defines an upper end 26, a lower end (not shown) opposite the upper end, and opposing sides 28. Handle 22 defines a necked-down gripping portion 30 at a location proximal the interface with cutting head 24. A pair of side cutouts 32 are formed in opposing sides 28, and a third cutout 34 is formed in the upper end 26. Cutouts 32 and 34 are substantially aligned, and ergonomically sized and shaped to be comfortably engaged by a user's thumb and other fingers. Advantageously, because gripping portion 30 is symmetrical, device 20 can be equally engaged by a user's left or right hand in one of several ergonomic positions.

Figure 2:
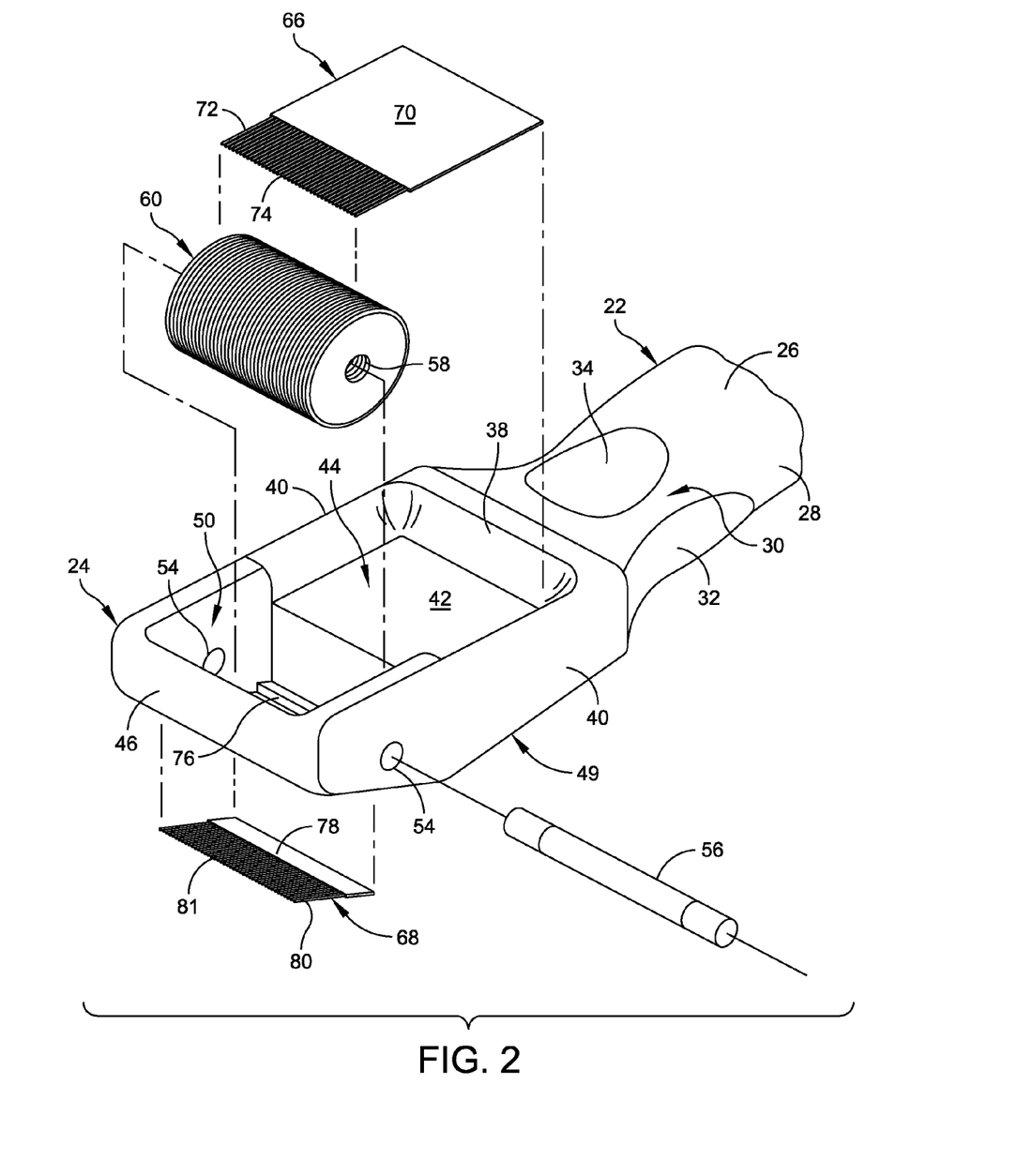
FIG. 2 is an assembly view of the components of the harvested dermal tissue processor illustrated in FIG. 1.

Referring also to FIG. 2, cutting head 24 is defined at its periphery by a frame that includes a laterally extending rear wall 38 attached to handle 22, and side walls 40 extending forwardly from opposite ends of rear wall 38. A collection plate 42 is disposed between side walls 40 and extends forwardly from rear wall 38 a distance less than the total length of side walls 40. It should be appreciated that plate 42 extends in a plane that is lower than the plane defined by the upper edges of rear and side walls 38 and 40. Accordingly, a receptacle 44 is formed from plate 42 along with walls 38 and 40 that receives processed tissue, as will be described in more detail below. A laterally extending front wall 46 connects the outer ends of side walls 40. A void 50 is thus defined at the front of the cutting head 24 by front wall 46, side walls 40, and collection plate 42.

Figure 5:
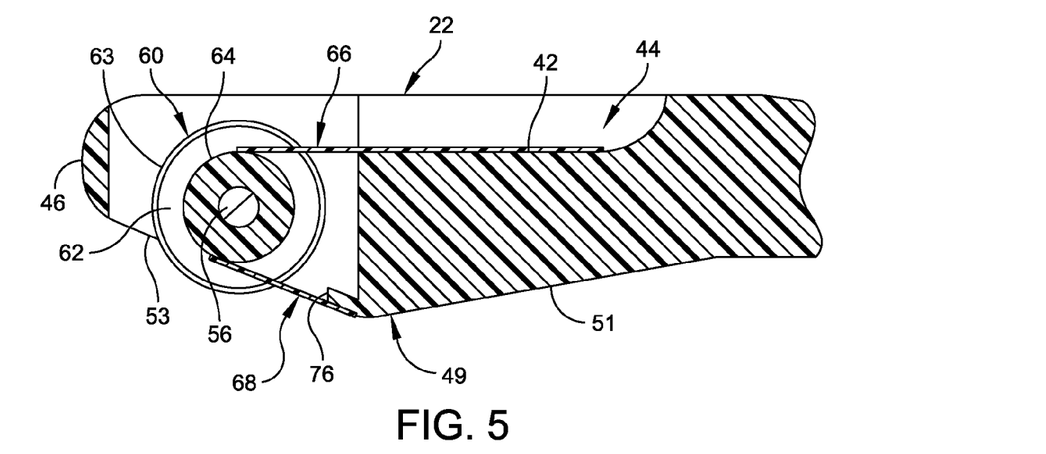
FIG. 5 is a sectional side elevation view of the harvested dermal tissue processor taken along line 5-5 of FIG. 3.
Figure 6:
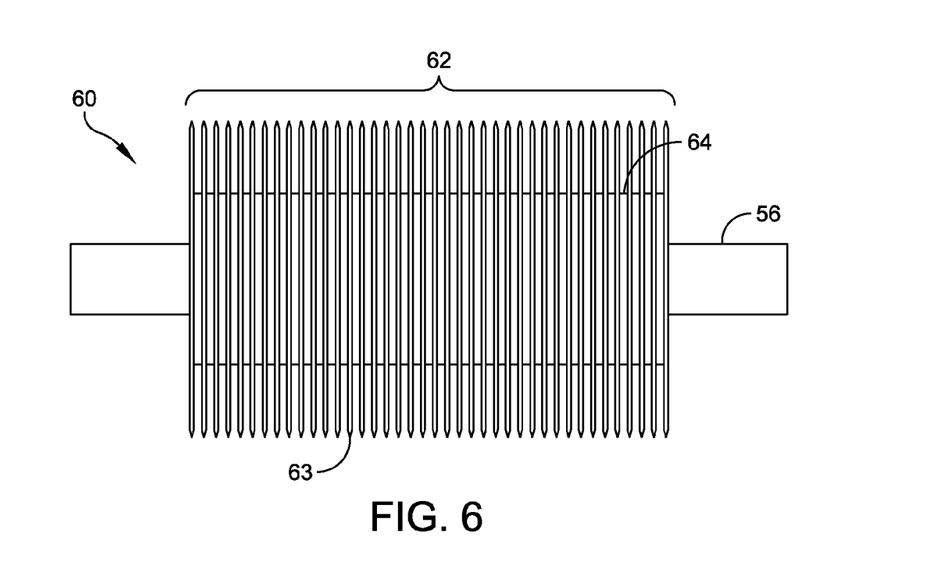
FIG. 6 is a side elevation view of a cutting assembly forming part of the harvested dermal tissue processor illustrated in FIG. 1.

Referring also to FIGS. 5 and 6, a cutting assembly 60 is disposed within void 50 at a position upstream from collection plate 42 with respect to the direction of processed tissue particle travel during operation. Cutting assembly 60 is formed from a plurality of generally circular metal cutting blades 62 spaced apart by a plurality of washers 64 interposed between adjacent blades 62. Each blade 62 converges at its periphery to a circular blade tip 63. Tips 63 can be formed with a double bevel, single bevel, or serrated or jagged edge. Washers 64 have a diameter less than the diameter of cutting blades 62 such that blade tips 63 extend outwardly from adjacent washers 64.

Cutting assembly 60 is rotatably supported by cutting head 24. In particular, a pair of aligned apertures 54 extends through the side walls 40 and receives a cylindrical axle 56. Axle 56 extends through the apertures 54, and receives a hub 58 extending centrally through cutting assembly 60. In accordance with the preferred embodiment, axle 56 is preferably rotatably fixed in apertures 54, and each blade 62 and washer 64 rotate independently around the axle 56. Alternatively still, blades 62 and washers 64 can be interlocked or otherwise fastened to each other such that each cutting blade 62 is rotatably fixed to all other cutting blades of cutting assembly 60. In this embodiment, the interlocked or fastened blades 62 and washers 64 can collectively rotate about axle 56, which is fixed within apertures 54. Alternatively still, the interlocked or fastened blades 62 and 64 can be fixed with respect to rotation about axle 56, and axle can be inserted into apertures 54 via traditional roller bearings (not shown) that enable axle 56 to rotate with respect to cutting head 22.

Washers 64 can assume any size, and preferably define a thickness between 100 microns and 5 mm. The distance between adjacent blade tips 63 is limited by the thickness of the corresponding blade 62 and washer 64, and is preferably within the range of 100 microns and 5 mm, and more preferably between 200 microns and 1200 microns.

While the cutting assembly 60 has been described in accordance with the preferred embodiment, a skilled artisan will appreciate that washers 64 could be eliminated such that blades 62 are disposed immediately adjacent each other, and the blade tips are spaced apart a distance equal to the thickness of each blade 62. It should be further appreciated that cutting assembly 30 could be formed from a single elongated annular member having a plurality of spaced apart blade tips formed in its outer surface. The present invention is not intended to be limited to any of these embodiments.

Cutting head 24 defines a wide V-shaped base 49 that includes the lower surface 51 of plate 42, and the lower surfaces 53 of side walls 40 at a location forward of plate. Lower surface 51 of plate 42 extends forward from rear wall 38, and slightly downwardly at an angle between 10 and 50 degrees with respect to the horizontal plane. Lower surface 53 is beveled at a location laterally aligned with void 50, and connect with lower surface 51. Lower surface 53 preferably defines an angle in the range of 10 and 50 degrees with respect to the horizontal plane, and preferably 30 degrees. Accordingly, device 20 can be tilted forwards to engage cutting assembly 60 with the harvested tissue that is to be processed.

Figure 7:
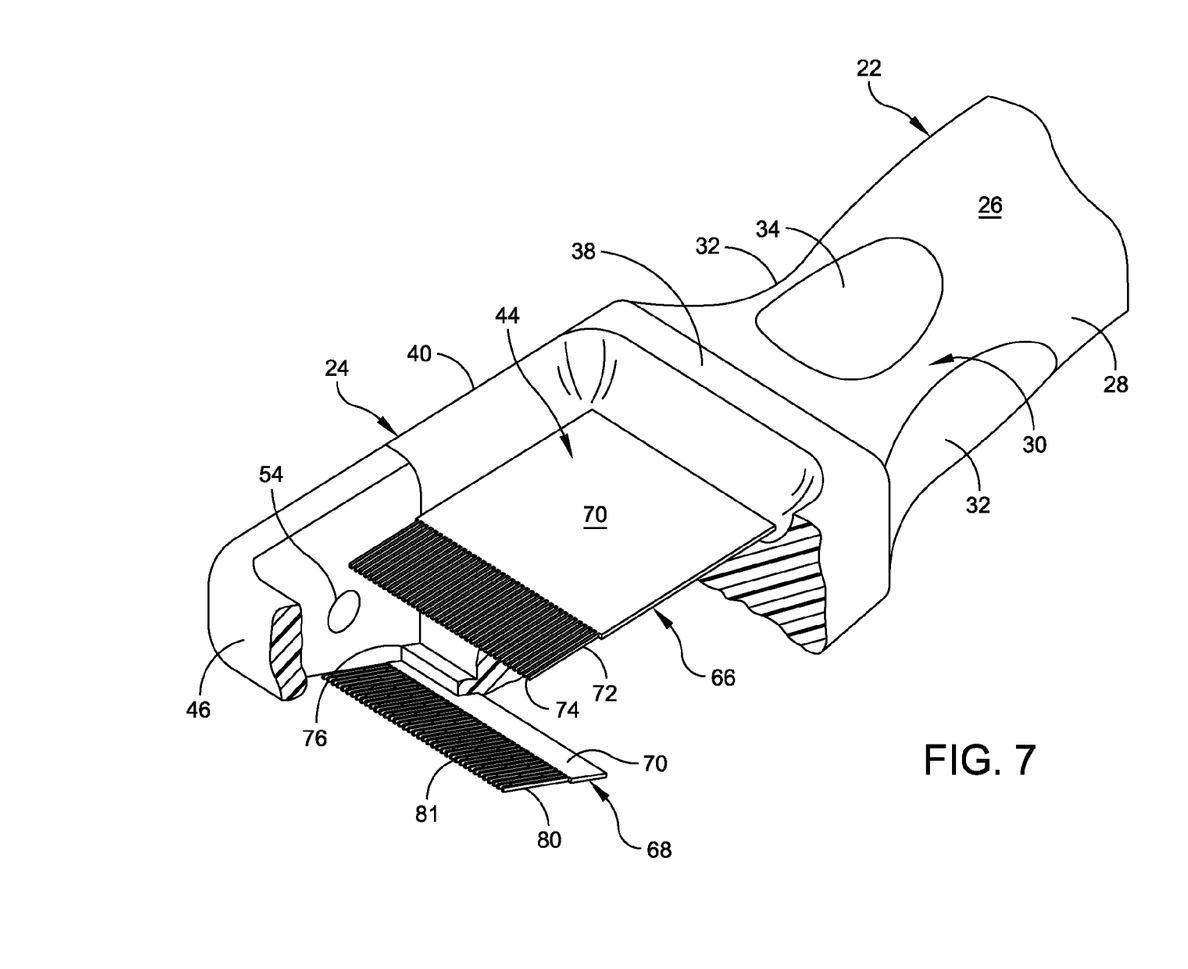
FIG. 7 is a perspective view of the harvested dermal tissue processor illustrated in FIG. 1 having a portion cut away.

Referring also to FIG. 7, an upper and a lower tissue separator 66 and 68, respectively, are fastened to cutting head 24 and engage cutting assembly 60 to remove tissue that may be disposed between adjacent blades 62 during cutting operations. Separators 66 and 68 are preferably formed from a metal, but could alternatively be formed from a plastic, ceramic, or other suitable material as appreciated by a skilled artisan.

Figure 3:
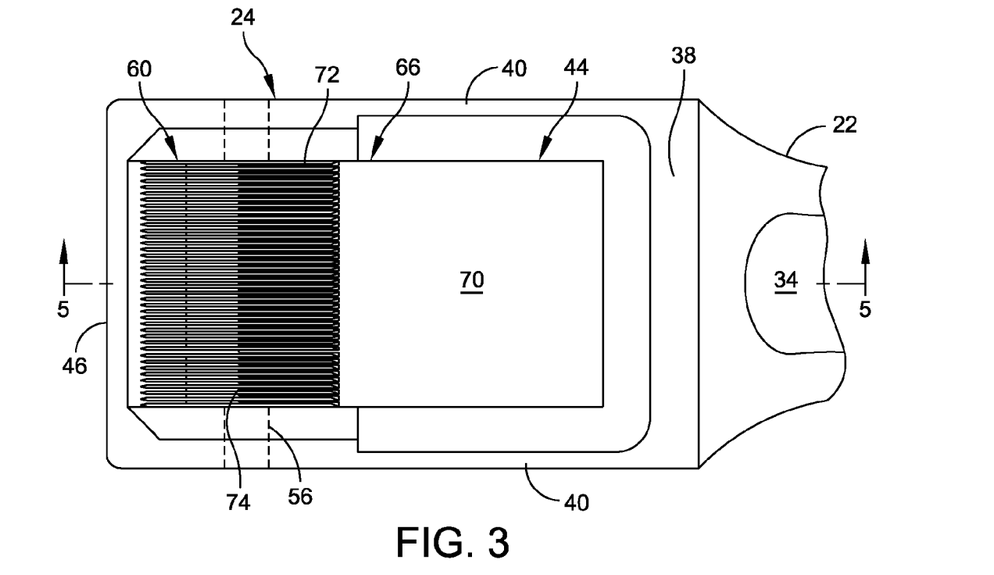
FIG. 3 is a top plan view of the harvested dermal tissue processor illustrated in FIG. 1.

Upper separator 66 is a comb-like structure that defines a laterally extending base 70 and a plurality of tines 72 extending forwardly from base 70. Tines 72 define a thickness that is preferably slightly less than the thickness between adjacent blades 62. Base 70 is mounted to the upper surface of collection plate 42 at a location such that adjacent tines 72 extend forwardly and interdigitate with corresponding adjacent blade tips 63 in a one-to-one relationship, as illustrated in FIG. 3. Tines 72 define distal ends 74 that ride along the outer surface of corresponding washers 64, preferably between the 12:00 and 2:00 position, and more preferably at approximately the 12:00 position. It should be appreciated that the present invention is not to be construed as limited to the position of tines 72 with respect to washers 64. Furthermore, if cutting assembly 60 does not include washers 64, tines would extend between blade tips 63 to a location where sliced particles would tend to accumulate.

Figure 4:
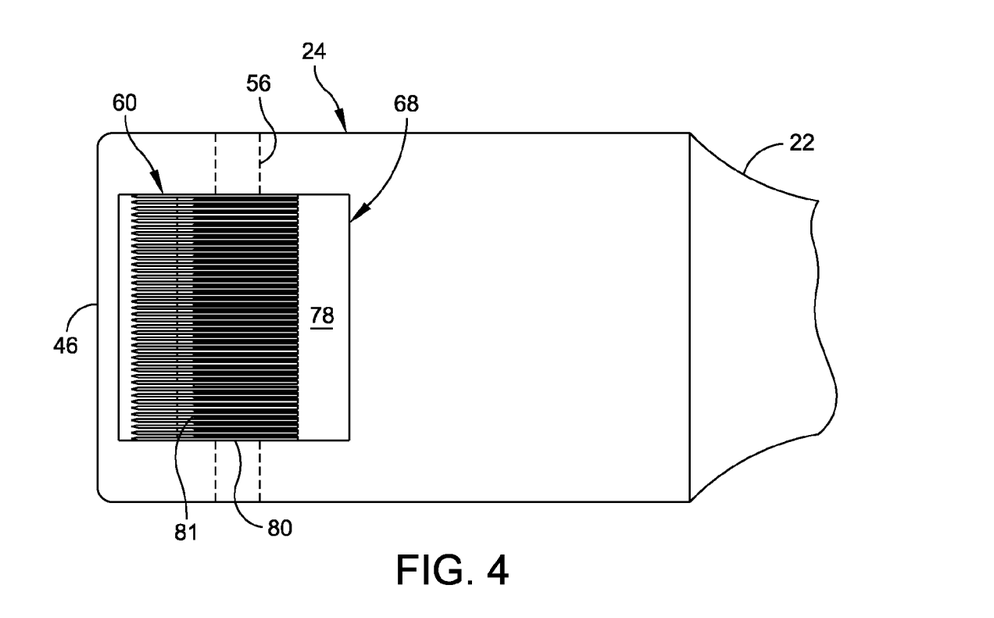
FIG. 4 is a bottom plan view of the harvested dermal tissue processor illustrated in FIG. 1.

A mounting flange 76 extends forwardly from lower surface 51 of plate 42, and slightly upwardly at an angle such that the lower surface of flange 76 extends along a plane that is tangential with respect to the outer periphery of washers 64. Flange 76 is preferably coplanar with lower surface 53. Lower separator 68 is a comb-like structure that defines a laterally extending base 78 and a plurality of tines 80 extending forwardly from base 78. Tines 80 define a thickness that is preferably slightly less than the thickness between adjacent blades 62. Base 78 is mounted to the lower surface of flange 76 such that adjacent tines 80 extend forwardly and interdigitate with corresponding adjacent blades 62 in a one-to-one relationship, as illustrated in FIG. 4. Tines 80 define distal ends 81 that ride along the outer surface of corresponding washers 64, preferably at a position between 6:00 and 7:00. It should be appreciated that the present invention is not to be construed as limited to the position of tines 80 with respect to washers 64. Furthermore, if cutting assembly 60 does not include washers 64, tines 80 would extend between blade tips 63 to a location where sliced particles would tend to accumulate.

Figure 12:
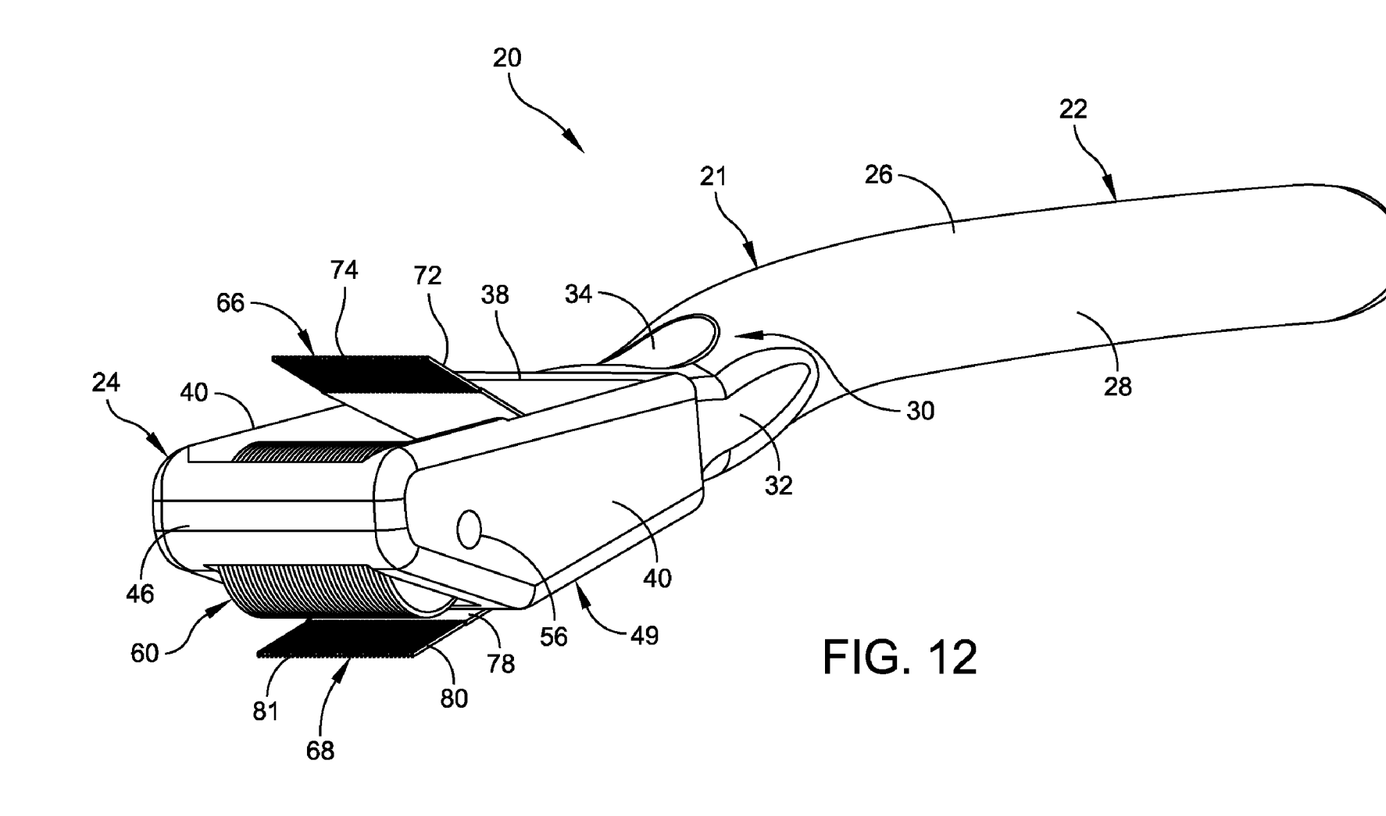
FIG. 12 is a perspective view of the harvested dermal tissue processor similar to the processor illustrated in FIG. 1 but having hinged tissue separators in accordance with an alternate embodiment.

In accordance with an alternative embodiment, either or both separators 66 and 68 can be actuated between a stand-by position, whereby tines 72 and 80 are removed from the interstices between adjacent blades 62, and an engaged position whereby tines 72 and 80 interdigitate with blades 62 as described above. For instance, referring to FIG. 12, bases 70 and 78 of separators 66 and 68, respectively, can be attached to cutting head 24 via a hinge (not shown), thus allowing the collection mechanism to be raised to the stand-by position, and lowered to the engaged position.

Figure 13:
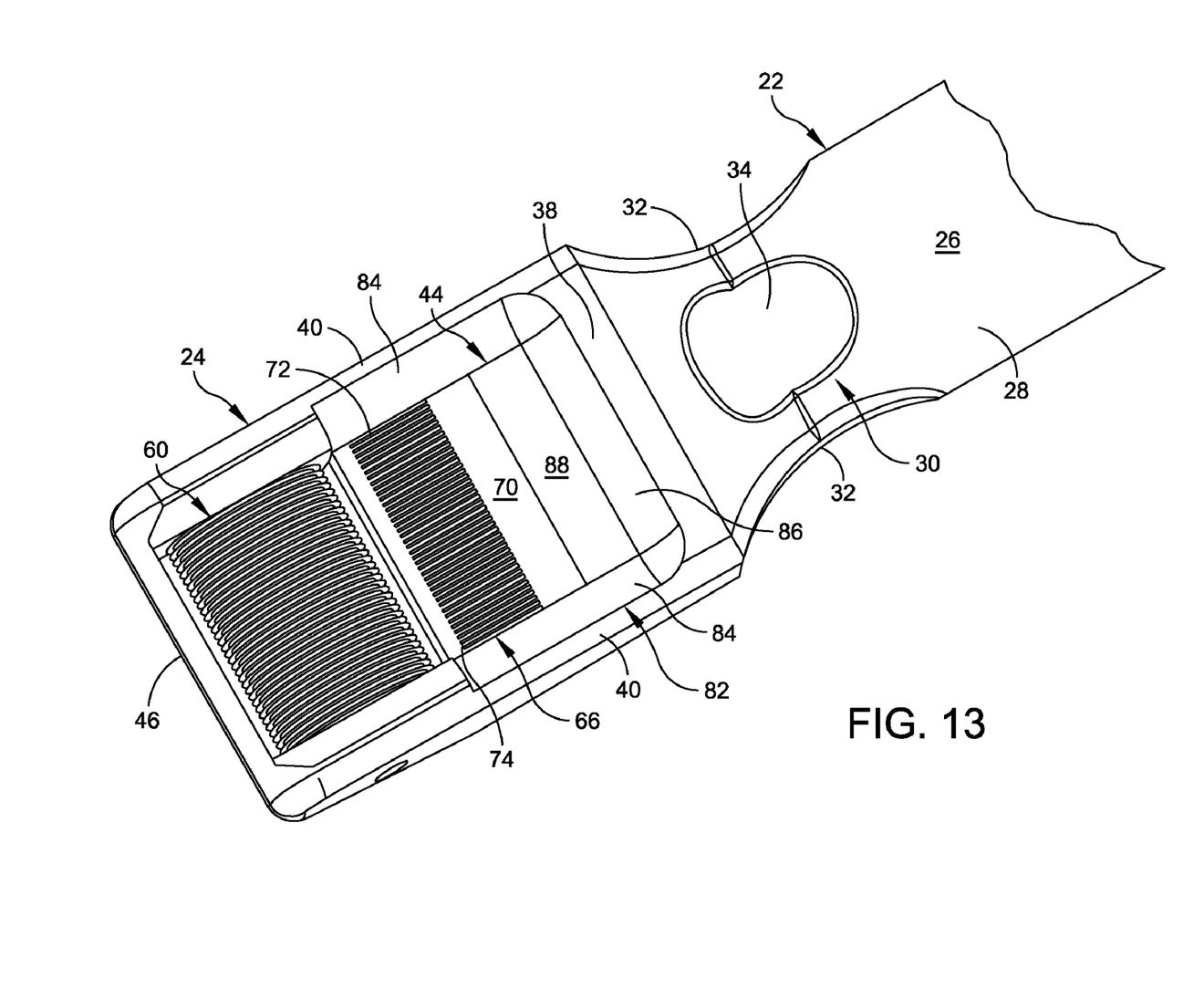
FIG. 13 is a perspective view of the harvested dermal tissue processor similar to the processor illustrated in FIG. 1, but including a slidable upper tissue separator in a stand-by position in accordance with an alternate embodiment.
Figure 14:
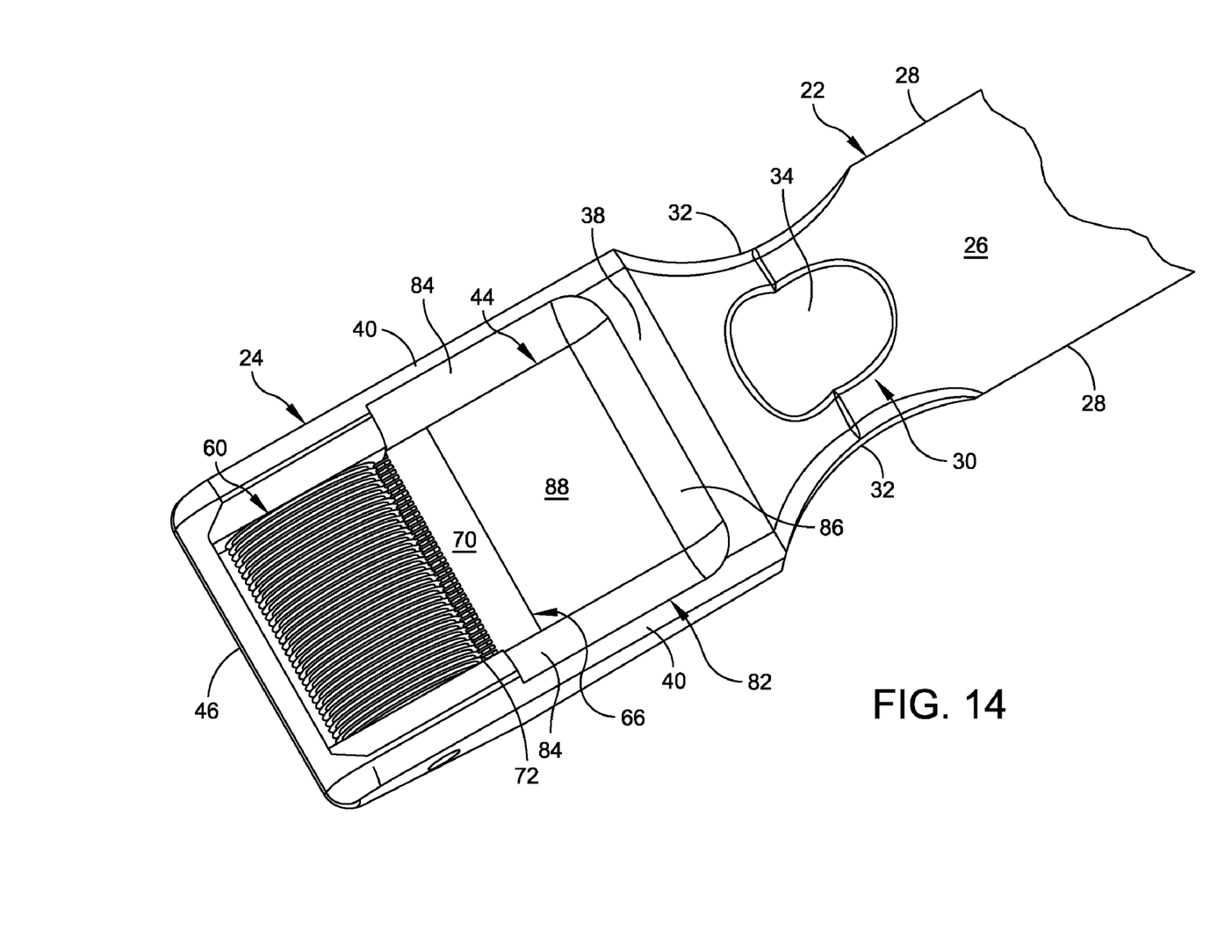
FIG. 14 is a perspective view of the harvested dermal tissue processor similar to FIG. 13, but with the tissue separator in an engaged position.

Alternatively still, referring to FIGS. 13 and 14, a receptacle can be attached to the upper surface of cutting head 24. Receptacle 82 includes a pair of opposing side walls 84 joined at their outer ends by a rear end wall 86. A recessed collection plate 88 extends between side walls 84 and forwardly from end wall 86, and receives processed tissue during operation of device 20. Upper separator 66 is coupled to receptacle 82, and rides along guide rails (not shown) that are carried by side walls 84. The guide rails are angled such that separator 66 can be translated backwards and forward from the stand-by position illustrated in FIG. 13 to the engaged position illustrated in FIG. 14. One or more detents can be formed in the guide rail and positioned to resist (though not prevent) translation of separator 66 away from both the stand-by and engaged positions. The detents enable a user to lock the separator 66 in the desired position during operation.

Figure 15:
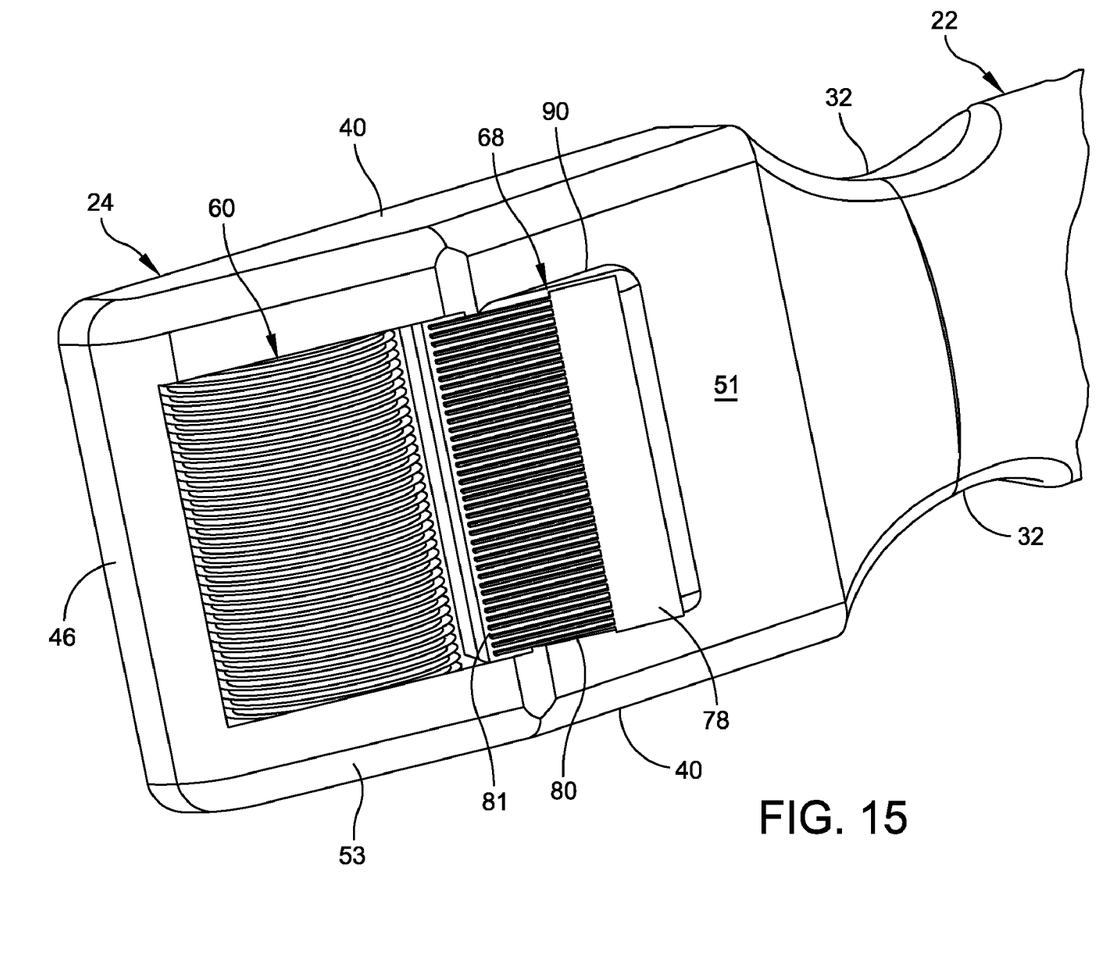
FIG. 15 is a perspective view of the harvested dermal tissue processor similar to the processor illustrated in FIG. 1, but including a slidable lower tissue separator in a stand-by position in accordance with an alternate embodiment.
Figure 16:
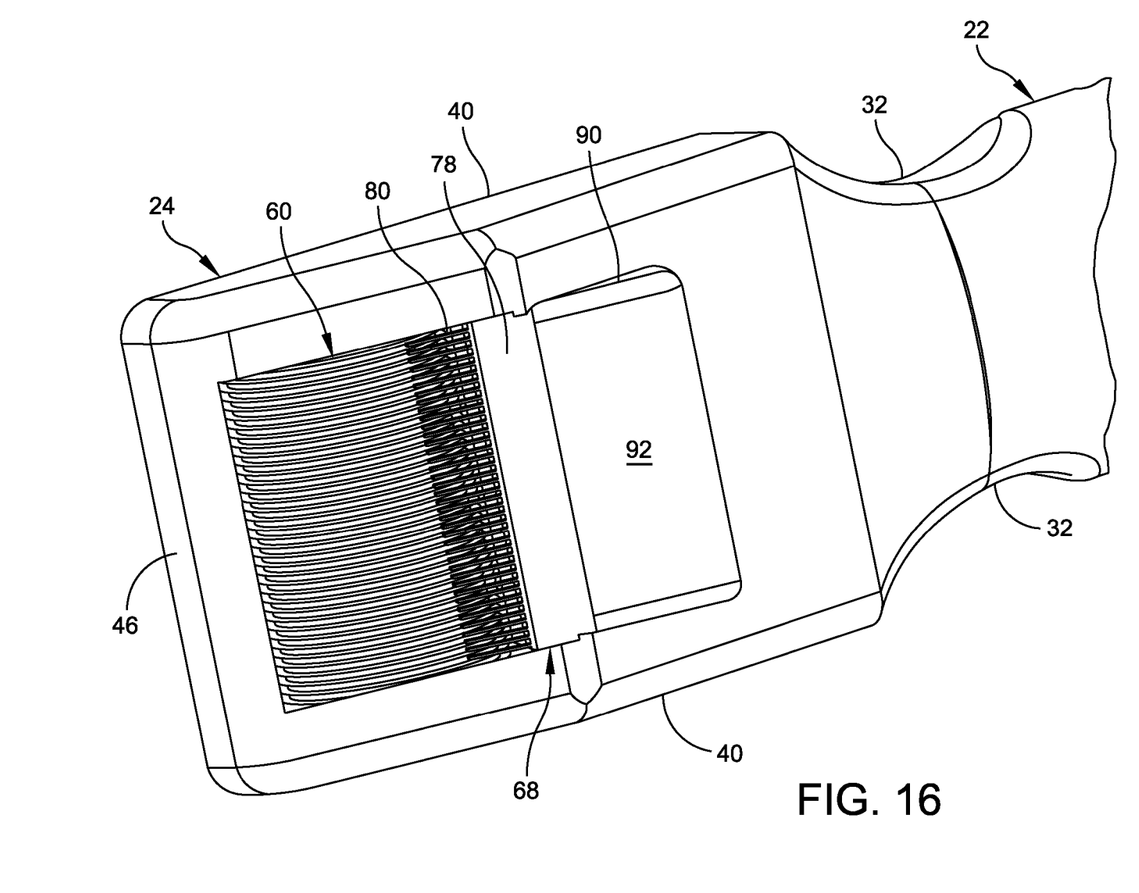
FIG. 16 is a perspective view of the harvested dermal tissue processor similar to FIG. 15, but with the tissue separator in an engaged position.

Referring to FIGS. 15 and 16, lower separator 68 can alternatively be mounted onto a ramp 90 that is attached to lower surface 51 of plate 42. Ramp 90 presents a ramp surface 92 that is angled towards washers 64. Separator 68 slidably rides along ramp surface 92 via guide rails (not shown) or the like, and can thus be translated from the stand-by position illustrated in FIG. 15 to the engaged position illustrated in FIG. 16. One or more detents can be formed in the guide rail and positioned to resist (though not prevent) translation of separator 68 away from both the stand-by and engaged positions. The detents enable a user to lock the separator 68 in the desired position during operation.

Advantageously, because device 20 lacks complex electrical components, it can be manufactured inexpensively compared to conventional dermal tissue processing devices.

Operation of dermal tissue processing device 20 will now be described with reference to FIGS. 8-11. As will become apparent from the description below, device 20 is capable of performing a forward and backward cutting operations.

Figure 8:
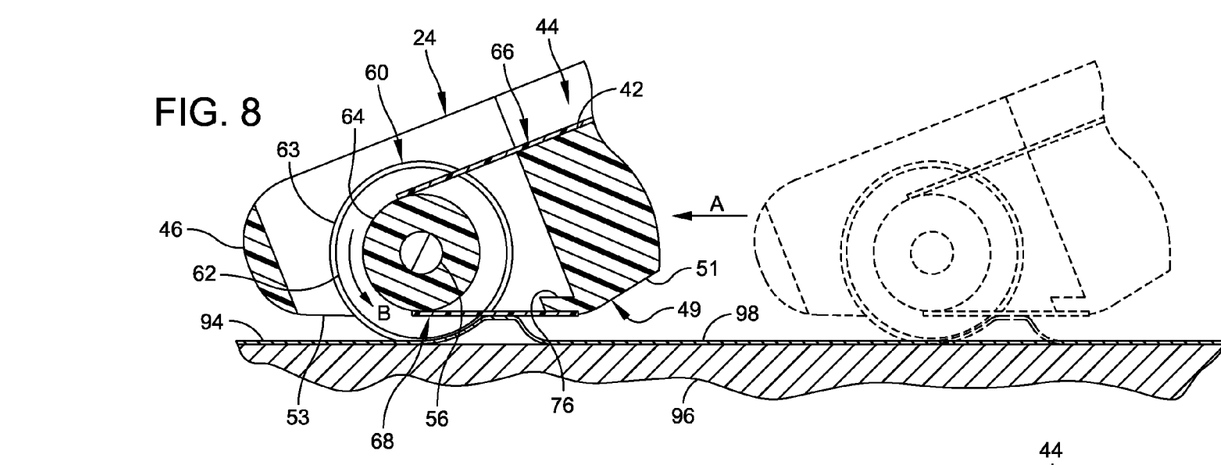
FIG. 8 is a sectional side elevation view of the harvested dermal tissue processor illustrated in FIG. 1 during a forward cutting operation.

Referring initially to FIG. 8, a sheet of harvested dermal tissue 94 is disposed on a cutting surface 96. Cutting surface 96 is preferably formed from a rubber, plastic, or other material suitable for supporting tissue 94 to be processed. It is desirable that surface 96 be sterile, sufficiently ductile and tacky to hold the tissue 94 in place and prevent slippage of the cutting blades 62, and durable to resist being cut by the blades during operation. Separators 66 and 68 (if movable) are then brought into engagement with cutting assembly 60.

With continuing reference to FIG. 8, device 20 is tilted up and forward at an angle approximately equal to the angle of beveled surface 53 such that both surfaces 51 and 53 are clear from interference with the cutting surface. Tilting the device 20 provides the user with increased leverage to apply downward force when performing cutting operations.

Device 20 is then lowered onto cutting surface 96 at a location immediately behind the tissue 94. The user applies a sufficient amount of downward force to enable cutting blades 62 to penetrate through tissue 94, and translates device 20 forward along the direction of Arrow A while maintaining engagement between blades 62 and cutting surface 96. The forward cutting operation thus ensues, whereby blades 62 thus rotate counterclockwise as indicated by Arrow B as they cut through the tissue 94.

Figure 9:
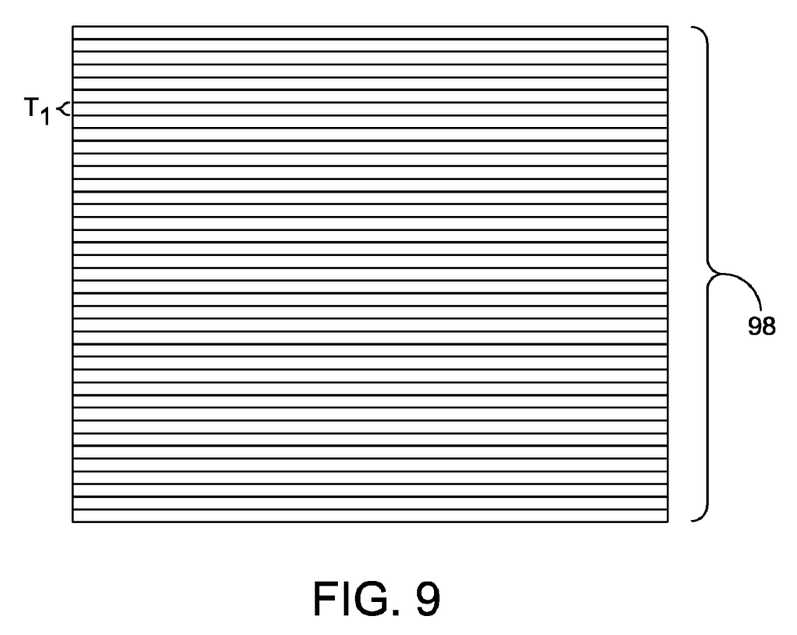
FIG. 9 is a schematic illustration of the harvested tissue after a first forward cutting operation.

Referring also to FIG. 9, the first forward cutting operation slices the tissue 94 into a plurality of adjacent fine strips 98 having a thickness TI substantially equal to distance between adjacent cutting blade tips 63. As blades 62 rotate during the forward cutting operation, sliced tissue 94 tends to become immediately lodged within the interstices between adjacent blades. The lodged strips 98 rotate along with blades 62 towards lower separator 68, and are brought into contact with the interdigitating tines 80. The tissue 94 rides along the lower cam surfaces of tines 80, becomes separated from cutting assembly 60, and falls back onto cutting surface 96 as substantially parallel strips 98. Lower separator 68 can be disengaged from cutting assembly 60 after the forward cutting operation, or blade can be rotated further counterclockwise, to force the distal ends of strips 98 onto the cutting surface 96. Multiple passes may be made if, for instance, the width of the harvested tissue 94 is greater than the distance between outer cutting blades 62.

Figure 10:
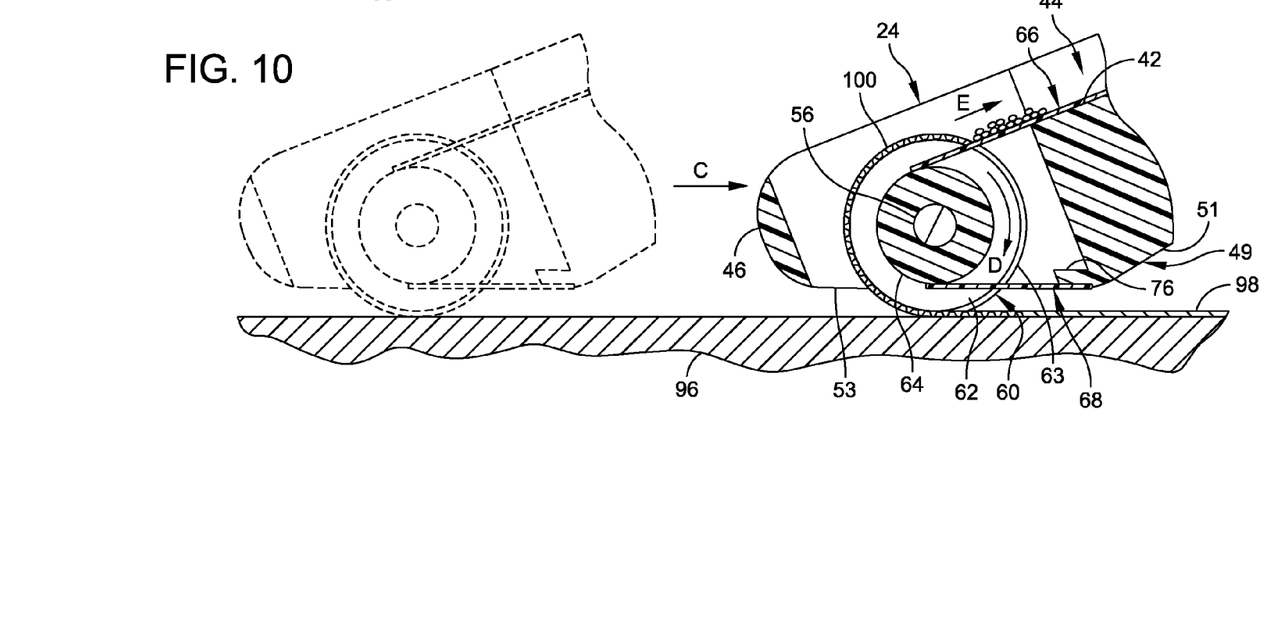
FIG. 10 is a sectional side elevation view of the harvested dermal tissue processor illustrated in FIG. 1 during a backward cutting operation.

Once the sheet of tissue 94 has been sliced and separated onto cutting surface 96, a backward cutting operation can be performed by orienting device 20 in a second direction, such as 90 degrees. 90 degree orientation is preferred such that the cutting direction extends substantially orthogonal with respect to the strips 98.

In particular, device 20 is positioned in front of strips 94, and lowered such that cutting assembly engages the front edge of the front-most strip. The user applies a sufficient amount of downward force to enable cutting blades 62 to penetrate through tissue 94. The backward cutting operation ensues, whereby device 20 is translated backwards along the direction of Arrow C while maintaining engagement between blades 62 and tissue 94. Blades 62 thus rotate clockwise as indicated by Arrow D.

Figure 11:
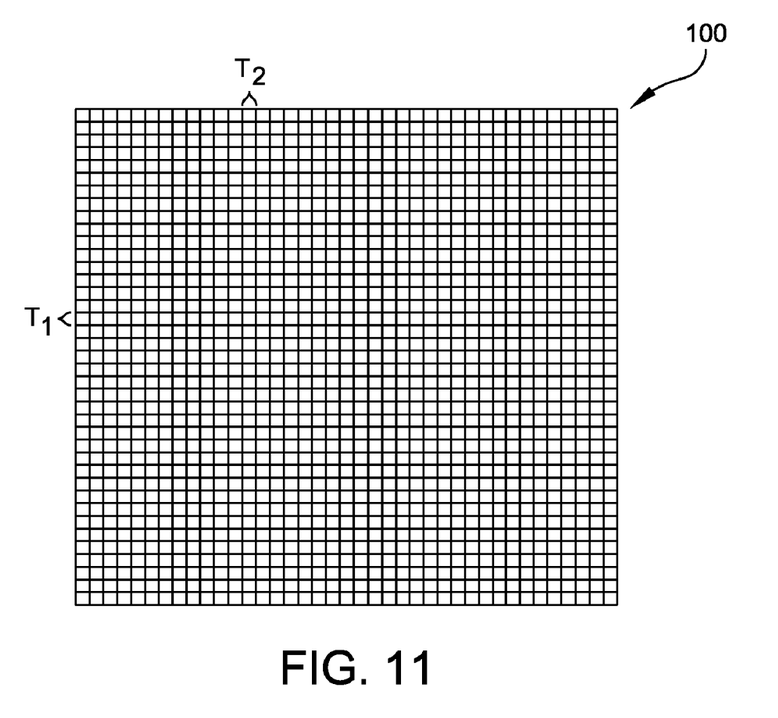
FIG. 11 is a schematic illustration of the harvested tissue after two cutting operations.

Referring also to FIG. 11, if the backward cutting operation is performed immediately after the first forward cutting operation, the tissue 94 is sliced into fine particles 100 defined by two dimensions T1 and T2, each of which being as small as the distance between adjacent blade tips 63. Particles 100 in FIG. 11 are illustrated schematically in a grid-like pattern to identify dimensions T1 and T2 of substantially square or rectangular particles. The particles 100, of course, would separate and travel into receptacle 82 after the first backward cutting operation, and may not form a perfect grid on the cutting surface after two sequential forward cutting operations. In this regard, it should be appreciated that multiple cutting operations can be performed, in which case sliced particles can assume any geometric configuration, regular or irregular, such as rectangles, triangles, and trapezoids. Dimensions T1 and T2 are therefore intended to be broadly construed to individually define the length of at least one of the edges of a particle of sliced tissue using device 20.

As blades 62 rotate clockwise during the backward cutting operation, particles 100 tend to become immediately lodged within the interstices between adjacent blades. The lodged particles 100 rotate along with blades 62 towards upper separator 66, and are brought into contact with the interdigitating tines 72. The lodged particles 100 accumulate on the upper surfaces of tines 72, and are pushed backwards onto collection plate 42 by incoming particles 100 along the direction of Arrow E. The particles may then be easily inspected by the user using a forceps or the like to determine whether the desired particle sizes have been achieved.

Upper separator 68 can be disengaged from cutting assembly 60 after the backward cutting operation to force the remaining particles 100 onto collection plate 42. Otherwise, if separator 68 is not movable, device 20 can be further translated along cutting surface 96 to ensure that all particles lodged in cutting assembly 60 engage the upper tines 72 and are removed. In rare instances, a tool can be inserted into the interstices between blades 62 and used to force the remaining particles 100 onto collection plate 42. Multiple backwards passes can be made if, for instance, strips 98 are longer than the distance between outer cutting blades 62.

After the first forward and backward cutting operations have been performed, particles 100 can define dimensions T1 and T2 within the range of 100 microns and 5 mm, and preferably between 200 and 1200 microns depending on the distance between adjacent blade tips 63.

In some instances, the user may wish to perform more than one forward and backward cutting operation. In this instance, after the first forward cutting operation has been performed, additional cutting operations in either direction can be performed as desired. A backward cutting operation can then be performed to accumulate the further sliced particles in receptacle 82. If, upon examination of the accumulated particles, the desired edge dimensions have not yet been achieved, the particles can be poured out of receptacle 82 onto cutting surface 96, and one or more additional cutting operations can be performed.

It has been found that particles having dimensions T1 and T2 between 100 and 1200 microns can be prepared using device 20. Transplanted particles as small as 100 to 1200 microns have been found to achieve better results than larger particles, as they enable increased expansion ratios. Once the desired particle size has been achieved, the processed tissue can be transplanted into a wound.

Advantageously, the present invention provides a dermal tissue processing device 20 that is portable, manually operated, and relatively inexpensive, thereby rendering the device 20 disposable after one use. The labor required to clean and sterilize conventional dermal tissue processors is thus avoided. It is further advantageous that the present device 20 can be positioned by the user in any desirable orientation relative to the tissue without having to adjust the position of the tissue. Device 20 thereby provides the user with enhanced cutting operation flexibility with respect to conventional devices. Furthermore, device 20 enables the operator to easily remove finely sliced particles from between adjacent blades 62.

Figure 17:
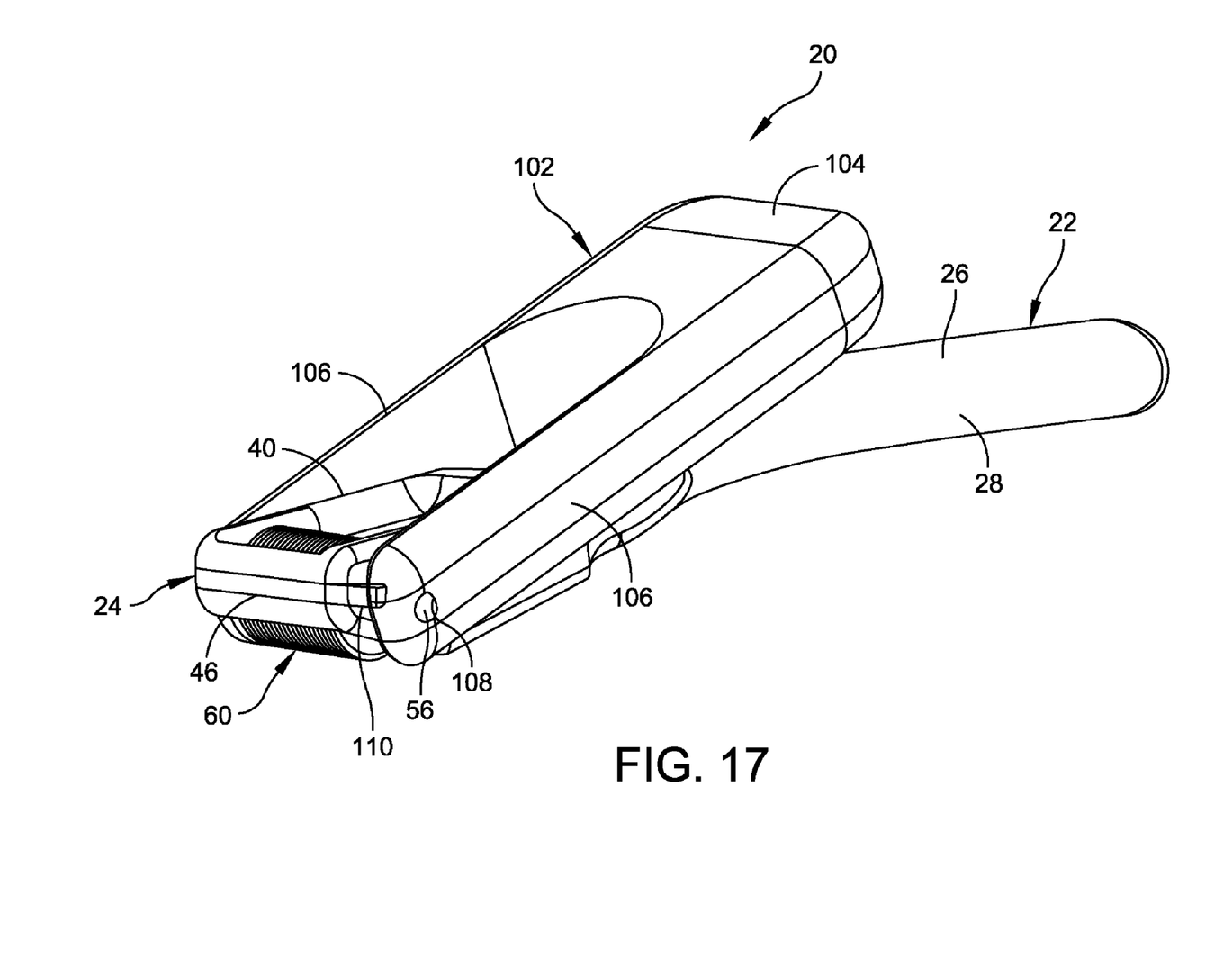
FIG. 17 is a perspective view of the harvested dermal tissue processor similar to the processor illustrated in FIG. 1, but including a second handle in a stand-by position in accordance with an alternate embodiment.
Figure 18:
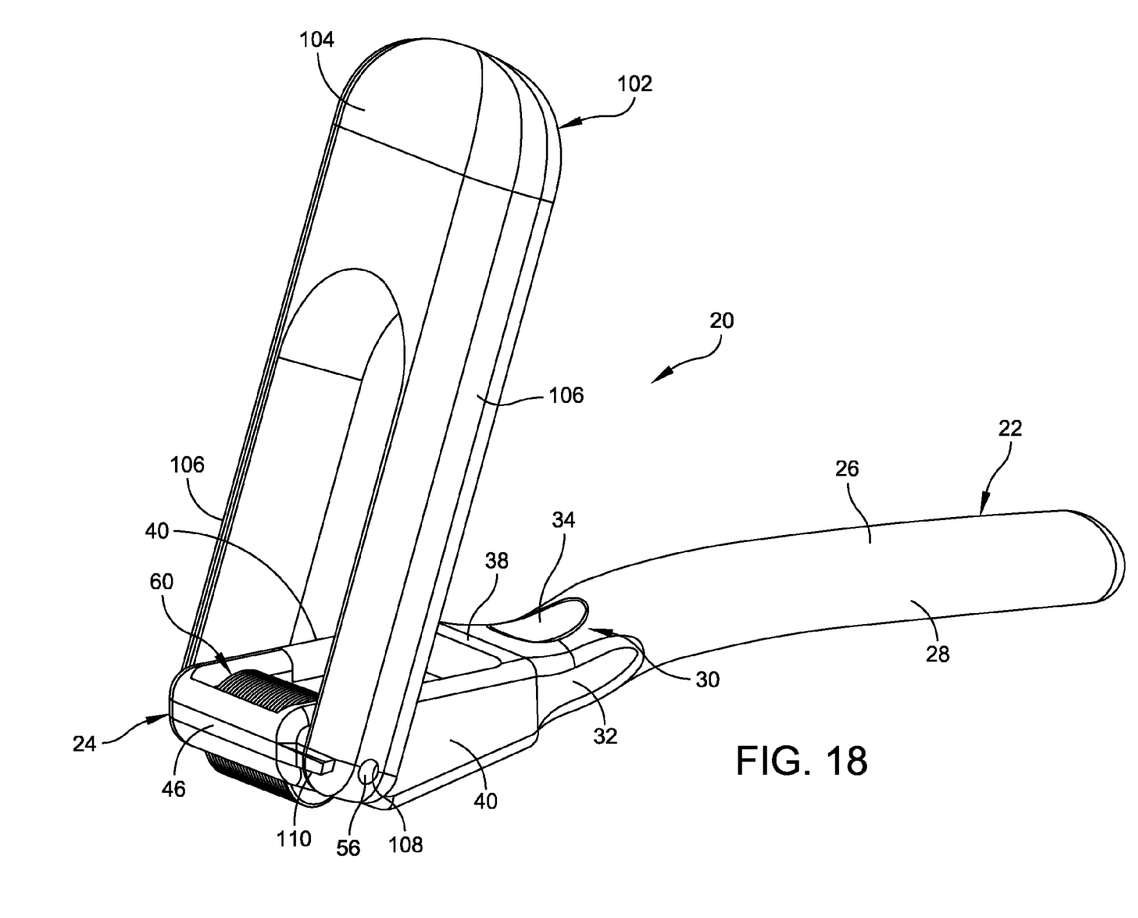
FIG. 18 is a perspective view of the harvested dermal tissue processor similar to FIG. 17, but with the second handle in an engaged position.

Referring now to FIGS. 17 and 18, an alternate embodiment of the present invention provides second handle 102 that can be connected to cutting head 24. Handle 102 presents a second surface that can be engaged by the user to provide greater leverage when applying downward pressure during cutting operations. Second handle 102, for instance, can define a gripping surface 104 connected to cutting head 24 via a pair of interconnecting legs 106. Each leg 106 can define an aperture 108 extending therethrough and aligned with apertures 54, such that axle 56 extends through both pairs of apertures 54 and 108. Second handle 102 can thus be pivoted from a flat storage position as illustrated in FIG. 17, whereby gripping surface 104 rests against handle 22, to an engaged position as illustrated in FIG. 18, whereby handle 102 extends substantially vertical. A flange 110 extends outwardly from front wall 46 and engages the forward surface of legs 106 when handle 102 is engaged to prevent over-rotation of the handle.

Alternatively, flange 110 can be configured to allow handle 102 to pivot to a position between the vertical position illustrated and a horizontal position on the opposite side of cutting head 24 with respect handle 22 to assist during forward cutting operations. Alternatively still, a second flange (not shown) can be provided that is selectively engaged and allows handle 102 to pivot to a position between the vertical and closed positions illustrated to assist during backward cutting operations.

The user can grip handle 22 with his or her dominant hand to guide the cutting direction, and engage second handle 102 with the other hand to apply additional downward force during the cutting operation.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements included within the spirit and scope of the invention, as set forth by the appended claims.

What is claimed is:

1. A method for processing tissue using a hand-held device having a housing that rotatably supports a plurality of spaced apart blades having tips, the method comprising:

bringing the blade tips into contact with the tissue such that the blade tips engage a cutting surface upon which the tissue is disposed;

translating the hand-held device along the cutting surface in a first direction to cut through the tissue to produce sliced tissue, the sliced tissue being removed from the spaced apart blades by a separator having a plurality of tines that interdigitate with the plurality of blades as the hand-held device is translated across the cutting surface in the first direction;

bringing the cutting blades into contact with the sliced tissue such that the blade tips engage the cutting surface; and translating the hand-held device along the cutting surface in a second direction to cut through the sliced tissue and produce further sliced tissue, the further sliced tissue being removed from the spaced apart blades by a second separator having a second plurality of tines that interdigitate with the plurality of blades as the hand-held device is translated across the cutting surface in the second direction.

2. The method of claim 1, wherein the second direction is opposite the first direction.

3. The method of claim 1, wherein the blades are spaced apart by spacer members having a diameter that is less than a diameter of the blades.

4. The method of claim 1, wherein the further sliced tissue is received in a receptacle defined by the housing of the hand-held device.

5. A method, comprising:
bringing a plurality of blade tips of an apparatus for processing harvested tissue into contact with the harvested tissue, the apparatus including:
a housing presenting a handle having a gripping surface and a cutting head attached to the handle,
a cutting assembly rotatably connected to the cutting head, the cutting assembly including the plurality of spaced apart blades having the blade tips, and
a first tissue separator having a plurality of tines that interdigitate with the plurality of spaced apart blades;
translating the apparatus along a cutting surface in a first direction to cut through the harvested tissue that is disposed on the cutting surface to produce sliced tissue, the sliced tissue being removed from the spaced apart blades by the plurality of tines of the first separator as the apparatus is translated across the cutting surface in the first direction;
bringing the plurality of blade tips into contact with the sliced tissue such that the blade tips engage the cutting surface; and
translating the apparatus along the cutting surface in a second direction to cut through the sliced tissue and create further sliced tissue, the further sliced tissue being removed from the spaced apart blades by a second separator having a second plurality of tines that interdigitate with the plurality of blades as the apparatus is translated across the cutting surface in the second direction.

6. The method of claim 5, wherein the second direction is opposite the first direction.

7. The method of claim 5, wherein the blades are spaced apart by spacer members having a diameter that is less than a diameter of the blades.

8. The method of claim 5, wherein the further sliced tissue is received in a receptacle defined by the housing of the apparatus after being removed by the second separator.

9. A method, comprising:
bringing a plurality of blade tips of a hand-held apparatus into contact with harvested tissue, the apparatus including:
a cutting head,
a cutting assembly disposed within the cutting head, the cutting assembly including a plurality of spaced apart blades including the blade tips, the blades configured to rotate with respect to the cutting head,
a first handle extending from the cutting head and providing a first gripping surface, and
a second handle pivotally coupled to the cutting head and providing a second gripping surface;
translating the hand-held apparatus along the cutting surface upon which harvested tissue is disposed in a first direction to cut through the harvested tissue to produce sliced tissue, the sliced tissue being removed from between the spaced apart blades by a plurality of tines of a first separator that interdigitate with the spaced apart blades as the hand-held apparatus is translated across the cutting surface in the first direction;
bringing the blade tips into contact with the sliced tissue such that the blade tips engage the cutting surface; and
translating the hand-held apparatus along the cutting surface in a second direction to cut through the sliced tissue and create further sliced tissue, the further sliced tissue being removed from the spaced apart blades by a second separator having a second plurality of tines that interdigitate with the plurality of blades as the hand-held apparatus is translated across the cutting surface in the second direction.

10. The method of claim 9, wherein the second direction is opposite the first direction.

11. The method of claim 9, wherein the blades are spaced apart by spacer members having a diameter that is less than a diameter of the blades.

12. The method of claim 9, wherein the further sliced tissue is received in a receptacle defined by the housing of the apparatus after being removed by the second separator.

* * * * *